United States Patent [19]

Welle et al.

[11] 4,081,552
[45] Mar. 28, 1978

[54] OXIME ETHERS HAVING ANTI-DEPRESSIVE ACTIVITY

[75] Inventors: Hendricus Bernardus Antonius Welle, Utrecht; Volkert Claassen, Weesp, both of Netherlands

[73] Assignee: U.S. Philips Corporation, New York, N.Y.

[21] Appl. No.: 668,454

[22] Filed: Mar. 19, 1976

[30] Foreign Application Priority Data

Mar. 20, 1975 Netherlands .......................... 7503311

[51] Int. Cl.² .................. A61K 31/15; A61K 31/275; C07C 121/78; C07C 131/00
[52] U.S. Cl. ................ 424/304; 260/465 E; 260/501.17; 260/566 AE; 424/316; 424/327
[58] Field of Search ................... 260/465 E, 566 AE; 424/304, 327

[56] References Cited

U.S. PATENT DOCUMENTS

3,692,835  9/1972  Van Dijk et al. ........... 260/465 E X

*Primary Examiner*—Dolph H. Torrence
*Attorney, Agent, or Firm*—Frank R. Trifari; Norman N. Spain

[57] ABSTRACT

Anti-depressive compounds of the formula

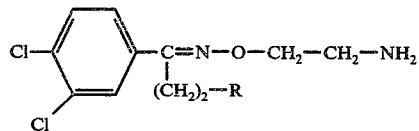

wherein R is $(CH_2)_p CN$, $(CH_2)_p O(CH_2)_q CH_3$ or $(CH_2)_r O(CH_2)OCH_3$ and $p = 1, 2$ or $3$ $q = 0$ or $1$ and $r = 0, 1$ or $2$.

13 Claims, No Drawings

OXIME ETHERS HAVING ANTI-DEPRESSIVE ACTIVITY

The invention relates to novel compounds having anti-depressive activity.

British patent specification No. 1,205,665 describes a large group of compounds having an anti-depressive, sedative and/or anti-convulsive activity. The anti-depressive activity of the known compounds may or may not be based on monoamino oxidase inhibition.

Compounds which inhibit monoamino oxidase are particularly difficult to handle. They often have serious side effects and they are often incompatible with other medicines and nitrients.

The regulations governing the use of medicines and which become more and more stringent ensure that only those compounds are considered for administration to human beings which are substantially free from noxious side effects.

It is the object of the invention to provide novel anti-depressive compounds whose activities are not based on monoamino oxidase inhibition and which in addition are substantially free from side effects.

It has been found that these requirements are fulfilled by compounds of formula

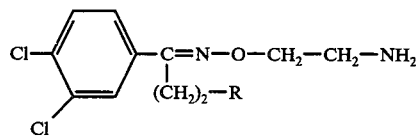

and their salts formed with pharmaceutically acceptable acids. In this formula, R represents the group $(CH_2)_pCN$, the group $(CH_2)_pO(CH_2)_qCH_3$, or the group $(CH_2)_rO(CH_2)_2OCH_3$ wherein $p$ is 1,2 or 3, $q$ is 1 if p is 1, while $q$ is 0 if $p$ is 2 or 3, and $r$ is 0, 1 or 2.

The anti-depressive activity of the compounds according to the invention is expressed both in a powerful potentiation of nor-adrenalin and in a strong serotonin potentiation. However, the compounds have no monoamino oxidase (MAO) inhibiting effect.

In contrast with structurally closely related compounds which are known from the above-mentioned British Patent Specification, the compounds according to the invention surprisingly give no stomach ulceration and bronchoconstriction.

The compounds according to the invention have a very low toxicity and neurotoxicity.

The following Table shows properties of the compounds of formula I and those of the best related known compound 3', 4'-dichloro hexanophenone O-(2-aminoethyl) oxime. HCl.

| Compound form. I R | salt of | noradr. pot. | serot. pot. | MAO inhib. | stomach ulcor. | broncho const. |
|---|---|---|---|---|---|---|
| $(CH_2)_1 CN$ | HCl | 5.5 | 8.4 | >215 | — | — |
| $(CH_2)_2CN$ | HCl | 10.0 | 14.0 | >215 | — | — |
| $(CH_2)_3CN$ | HCl | 4.3 | 31 | >215 | — | — |
| $CH_2-O-CH_2CH_3$ | HCl | 3.6 | 12 | >215 | — | — |
| $(CH_2)_2-O-CH_3$ | HCl | 2.9 | 25 | >215 | — | — |
| $(CH_2)_3-O-CH_3$ | HCl | 2.8 | 28 | >215 | — | — |
| $O(CH_2)_2-O-CH_3$ | maleic ac. 1:1 | 7.9 | 20 | >215 | — | — |
| $CH_2-O-(CH_2)_2OCH_3$ | fumaric.ac. 1:1 | 7.7 | 35 | >215 | — | — |
| $(CH_2)_2O(CH_2)_2OCH_3$ | fumaric ac. 1:1 | 7.1 | 37 | >215 | — | — |
| $(CH_2)_2CH_3$ | HCl | 2.5 | 10 | >215 | + | + |

The numbers in these Tables are $ED_{50}$ values, expressed in mg/kg.

The above data were determined in the following tests.

The noradrenalin potentiation was determined in the tetrabenazine test. In this test a quantity of the compound to be tested was administered orally to five male albino mice. After 45 minutes the animals were injected subcutaneously with 80 mg/kg of tetrabenazine. After another 45 minutes the degree of ptosis was determined and compared with the ptosis of animals which had received tetrabenazine only. The $ED_{50}$ was determined from the results.

The serotonin potentiation was determined in the 5-hydroxytryptophan test. For this purpose, the compounds to be tested were administered orally in a series of dosages to isolated male albino mice (5 mice per dosage) 1 hour prior to intraperitoneal administration of 150 mg/kg of dl-5-hydroxytryptophan. 30 Minutes after this threshold dosage the mice were observed individually and the following parameters were scored:

stereotypical shaking of the head, spreading of the hindlegs, tremor, tendency to flee, lordosis, clonic stamping with the front legs. The $ED_{50}$ value was calculated from the results.

The monoamino oxidase (MAO) inhibiting effect was determined in experiments in which a quantity of the compound to be tested was administered orally to five male albino mice. One hour later the animals were injected subcutaneously with tryptamine hydrochloride in a quantity of 250 mg/kg. This quantity does not cause mortality in animals which did not receive the compound to be tested, but did cause mortality in aniamls to which an active substance had been administered. Eighteen hours after the administration of tryptamine hydrochloride it was determined how many treated animals had died. The $ED_{50}$ was determined from the results.

By means of the method by Metysovà, Arzneimittelforschung 13 - 1039 (1963) it was determined whether the oral administration of 200 mg of a compound to be tested causes stomach ulceration.

By means of the method of Konzett-Rössler, Arch. Exp. Path. Pharmakol. 195 71 (1940) it was investigated whether a compound to be tested causes bronchoconstriction after intravenous administration of 3 mg/kg. Reduction of the breathing function as a result of bronchoconstriction is expressed in this method in a smaller volume of air taken in.

On the basis of their properties the compounds of formula I and their salts are particularly suitable for use in the treatment of neurotic and psychotic disturbances.

In these cases the compounds may be used in the treatment of depressive patients.

The quantity, the frequency and the way in which the substances are administered may vary in accordance with the individual patient and also the nature and the severity of the disturbances. In general, adults will receive a daily dose of from 25 to 500 mg orally. As a rule, a quantity of from 50 to 200 mg will be sufficient.

The compounds are preferably used in the form of injection liquids, pills, tablets, coated tablets, capsules, powders and the like. The compounds may be processed to such compositions according to methods which are known per se.

The invention therefore also relates to compositions having a compound of formula I or a salt thereof as an active constituent, and to methods to prepare such compositions, for example, by mixing an active substance with or dissolving it in solid or liquid pharmaceutical carrier materials.

As examples of pharmaceutically acceptable acids with which compounds of formula I can form salts may be mentioned inorganic acids, for example: hydrochloric acid, sulphuric acid, nitric acid; organic acids, such as citric acid, fumaric acid, tartaric acid, acetic acid, benzoic acid, maleic acid and the like.

The compounds of formula I and their salts may be prepared according to methods which are known for the preparation of this type of compounds and according to methods analogous thereto. The invention also relates to the preparation of the compounds.

The compounds can be obtained inter alia by reaction of a compound of formula II,

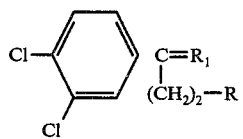

in which R has the above meaning and $R_1$ is an oxygen atom, an oxime group or an alkylene dioxy group, for example, ethylene dioxy, with a compound of formula III

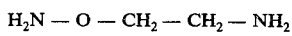

or a salt thereof. The reaction is preferably carried out in an inert solvent, for example, alcohols, dioxan, dimethylformamide, tetrahydrofuran, mixtures thereof, at temperatures between room temperature and the boiling point of the mixture, if desired in the presence of a base, for example pyridine.

Another method consists of a reaction between a compound of formula IV,

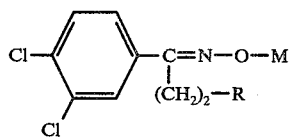

in which R has the above meaning and M is a hydrogen atom or an alkali metal atom, and a compound of formula V

or a salt thereof, in which Hal is a halogen atom, preferably chlorine or bromine.

The reaction is preferably carried out in an inert solvent, for example, alcohols, ethers or dimethylformamide. In the case in which M is a hydrogen atom, an acid binder is preferably added, for example, an alcoholate. The reaction temperature as a rule is between 0° and 50° C.

The compounds can also be prepared by reacting a compound of formula VI,

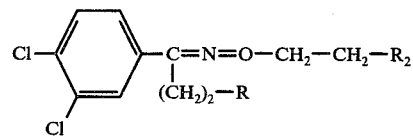

in which R has the same meaning as in formula I and $R_2$ is a mesyloxy group or a tosyloxy group, with ammonia. The reaction is preferably carried out in a solvent, for example an alcohol, usually at temperatures between room temperature and 150° C.

The starting compounds of formula VI are prepared by reacting a compound of formula IV with ethylene oxide in ethanol and in the presence of an alcoholate at temperatures up to 60° C. The reaction product is then converted into a compound of formula VI with tosyl chloride or mesyl chloride, in a solvent, for example, methylene chloride and possibly an acid binder, for example pyridine.

Another method of preparing the compounds of formula I consists of the reaction of a compound of formula VIII

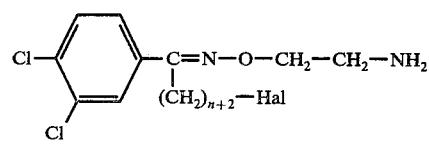

with a compound of formula VIII M'-R'. In these formulae, Hal is a chlorine atom or a bromine atom, $n$ has the value 0, 1, 2 or 3, M' denotes an alkali metal atom and R' has the meaning —CN, $O(CH_2)_qCH_3$ or $OC_2H_4OCH_3$. The reaction is preferably carried out in an inert solvent, for example ethanol, dimethylsulfoxide or dimethylformamide. The reaction temperature is between 0° and 70° C.

The compounds of formula I, in which R contains an oxygen atom, may also be obtained by reacting a compound of formula IX

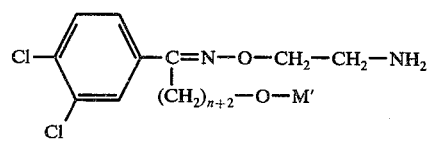

with a compound of formula X $R_3$-R". In these formulae, $n$ has the value 0, 1, 2 or 3, $R_3$ is a chlorine atom or a bromine atom or $(SO_4)_{1/2}$, M' is an alkali metal atom and R" is the group $(CH_2)_2OCH_3$ or the group $(CH_2)_qCH_3$. The reaction is preferably carried out in an inert solvent, for example, toluene or dimethylformamide. As a rule the reaction takes place at a temperature between 0° and 80° C.

The compounds of formula I, in which R contains an oxygen atom, may also be prepared by reducing a compound of formula XI

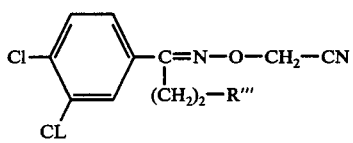

In this formula, R''' is a group $(CH_2)_p O(CH_2)_q CH_3$ or a group $(CH_2)_r O(CH_2)_2 OCH_3$, wherein $r = 0$, 1 or 2. The reaction may be carried out with a reduction agent, for example, a metal hydride, for example, lithium aluminium trimethoxyhydride, in a solvent, for example, tetrahydrofuran, dioxan and the like, at temperatures between 0° and 25° C.

The compounds of formula I may also be obtained by converting a compound of formula XII

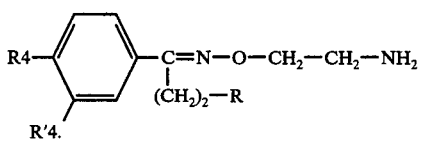

in which R has the same meaning as in formula I and one of the symbols $R_4$ and $R'_4$ represents an amino group and the other a chlorine atom, with nitrous acid and hydrochloric acid, and converting the reaction product with copper or cuprochloride.

The first step of this reaction is generally carried out in an excess of dilute hydrochloric acid at $-10°$ to $+5°$ C. The second step is carried out as a rule by the addition to copper or cuprochloride at temperatures between 20° and 75° C.

The compounds of formula I and their salts may also be prepared by hydrolyzing a compound of formula XIII

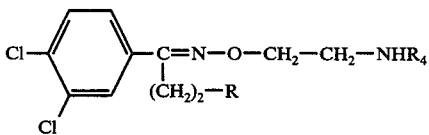

or a salt thereof. In this formula, $R_4$ is a protective group, for example, a trityl group. The reaction may be carried out in a water-mixed inert solvent, in acid conditions, at a temperature between room temperature and 100° C.

EXAMPLES

1. 3', 4'-dichloro-4-cyanobutyrophenone O-(2-aminoethyl) oxime hydrochloride A mixture of 6.9 mmol (1.67 g) of 3', 4'-dichloro-4-cyanobutyrophenone (melting point 53°-54° C), 6.9 mmol (1.03 g) of 2-aminooxyethylamine dihydrochloride, 6.9 mmol (0.56ml) of pyridine and 5 ml of absolute ethanol was refluxed for 3.5 hours.

The resulting residue was dissolved in 15 ml of water after evaporating the alcohol in vacuo. The resulting solution was rendered alkaline with 10 ml of 2N sodium hydroxide solution and then extracted three times with 10 ml of methylene chloride. The residue which was obtained, after drying the collected methylene chloride extracts over sodium sulphate and removing the solvent in vacuo, was dissolved in absolute ethanol, after which an equivalent quantity of alcoholic hydrochloric acid was added. The resulting solution was evaporated to dryness in vacuo, the residue was evaporated to dryness with 50 ml of isopropanol and then dissolved in 15 ml of isopropanol. After the addition of 35 ml of ether, the above entitled compound crystallized. The melting point was 129°-130° C.

2. 3', 4'-dichloro-5-cyanovalerophenone O-(2-aminoethyl) oxime hydrochloride A mixture of 7.2 mmol (1.85 g) of 3', 4'-dichloro-5-cyanovalerophenone (melting point 49°-51° C), 7.2 mmol (1.08 g) of 2-aminooxyethylamine dihydrochloride, 1.0 ml of pyridine and 7 ml of absolute ethanol was refluxed for 3 hours. The reaction mixture was then further processed in a manner identical to that described in Example 1. After crystallization from an ethanol-ether mixture the above entitled compound was obtained with a melting point of 134°-135° C.

3. 3', 4'-dichloro-6-cyanohexanophenone O-(2-aminoethyl) oxime hydrochloride A mixture of 8.1 mmol (2.19 g) of 3', 4'-dichloro-6-cyanohexanophenone, 8.1 mmol (1.21 g) of 2-aminooxyethylamine dihydrochloride, 8.1 mmol (0.65 ml) of pyridine and 5 ml of absolute ethanol was refluxed for 3.5 hours. The residue obtained after evaporating the ethanol in vacuo was crystalline. It was dissolved in 10 ml of warm absolute ethanol. After diluting said solution with 25 ml of ether the above entitled compound crystallized. melting point 131°-132° C.

4. 3', 4'-dichloro-4-ethoxybutyrophenone O-(2-aminoethyl) oxime hydrochloride A mixture of 4.6 mmol (1.20 g) of 3', 4'-dichloro-4-ethoxybutyrophenone (melting point 52°-54° C), 4.7 mmol (0.70 g) of 2-aminooxyethylamine dihydrochloride, 2.5 ml of pyridine and 5 ml of absolute ethanol was refluxed for 2.5 hours. The reaction mixture was evaporated to dryness in vacuo and the residue was dissolved in 40 ml of water. This solution was washed twice with 15 ml of petroleum ether (boiling point 40°-60° C), rendered alkaline with 10 ml of 2N sodium hydroxide solution and then extracted three times with 20 ml of ether. After washing the collected ether extracts with 10 ml of water and drying over sodium sulphate, the ether was evaporated in vacuo. The resulting base was then evaporated to dryness three times with 20 ml of toluene. Subsequently the hydrochloride was prepared by means of alcoholic hydrochloric acid. This was recrystallized from an ether/petroleum ether mixture. The melting point of the resulting above entitled compound was 92°-94° C.

5. 3', 4'-dichloro-5-methoxyvalerophenone O-(2-aminoethyl) oxime hydrochloride A mixture of 14 mmol (3.65 g) of 3', 4'-dichloro-5-methoxyvalerophenone, 14 mmol (2.1 g) of 2-aminooxyethylamine dihydrochloride, 7 ml of pyridine and 14 ml of absolute ethanol was refluxed for 2 hours. The reaction mixture was then further processes as described in Example 4. After crystallization from a mixture of ether and petroleum ether (boiling point 40°-60°

C) the above entitled compound was obtained with a melting point of 93°–94° C.

6. 3', 4'-dichloro-6-methoxyhexanophenone O-(2-aminoethyl) oxime hydrochloride.

The above entitled compound with a melting point of 82°–84° C (ether/petroleum ether) was obtained in an identical manner from 3', 4'-dichloro-6-methoxyhexanophenone and 2-aminooxyethylamine dihydrochloride.

7. 3', 4'-dichloro-3-(2-methoxyethoxy) propiophenone O-(2-aminoethyl) oxime maleate (1 : 1)

In an identical manner, 10 mmol (2.8 g) of 3', 4'-dichloro-3-(2-methoxyethoxy)propiophenone were converted with 10 mmol (1.5 g) of 2-amino-oxyethylamine dihydrochloride. The resulting base was converted with an equimolar quantity of maleic acid into the above entitled compound which was obtained as a resin.

8. 3', 4'-dichloro-4-(2-methoxyethoxy)butyrophenone O-(2-aminoethyl) oxime fumarate (1 : 1)

In an identical manner, 3', 4'-dichloro-4-(2-methoxyethoxy) butyrophenone was converted with an equimolar quantity of 2-amino-oxyethyl amine dihydrochloride. The resulting base was converted into the above entitled compound with an equimolar quantity of fumaric acid. After recrystallization from ethanol-acetonitrile 2/3, the melting point was 142°–143° C.

9. 3', 4'-dichloro-5-(2-methoxyethoxy)valerophenone O-(2-aminoethyl)oxime fumarate (1 : 1)

The title compound with a melting point of 141°–143° C was obtained in an identical manner from 3', 4'-dichloro-5-(2-methoxyethoxy) valerophenone and 2-amino-oxyethylamine dihydrochloride.

10. 3'-4'-dichloro-6-methoxyhexanophenone O(-2-aminoethyl) oxime hydrochloride 1.0 mmol (0.58 g) of 3', 4'-dichloro-6-methoxyhexanophenone O-(2-tritylaminoethyl) oxime was dissolved in 5 ml of 90% acetic acid and stored at room temperature for 3 days. The residue obtained after evaporation in vacuo was dissolved in 10 ml or ether. This solution was extracted with 10 ml or 0.1 N hydrochloric acid and this extract, after having been rendered alkaline with sodium hydroxide solution, was extracted with methylene chloride. These extracts were dried over sodium sulphate and then evaporated to dryness in vacuo. The resulting free base was converted into the above entitled compound with alcoholic hydrochloric acid. After crystallisation from ether/petroleum ether, the melting point was 82°–84° C.

11. 3', 4'-dichloro-6-cyanohexanophenone O-(2-aminoethyl) oxime hydrochloride

The above entitled compound having a melting point of 131°–132° C (ethanol/ether) was obtained in an identical manner from 3', 4'-dichloro-6-cyanohexanophenone O-(2-tritylaminoethyl) oxime.

12. 3', 4'-dichloro-4-cyanobutyrophenone O-(2-aminoethyl) oxime hydrochloride 5.0 mmol (1.29 g) of 3', 4'-dichloro-4-cyanobutyrophenone oxime (melting point 122°–123° C), 5.2 mmol (0.60 g) of 2-chloroethylamine hydrochloride and 0.7 g of powdered potassium hydroxide were added, in this sequence and while stirring at 10° C, to 12 ml of dimethylformamide (D.M.F). After stirring for 2 days at room temperature the D.M.F. was evaporated invacuo, the residue was brought in water and 2N hydrochloric acid was then added while stirring until pH 3. The remaining oxime was removed by means of ether. The acid aqueous solution was then rendered alkaline with 15 ml of 2N sodium hydroxide solution and then extracted three times with ether. After washing with a 5% sodium bicarbonate solution, drying over sodium sulphate and evaporating the ether, the free base was obtained. This was dissolved in alcoholic hydrochloric acid. After evaporating the ethonal, the above entitled compound was crystallized from isopropanol/ether (1 : 1). Melting point 129°–130° C.

13. 3', 4'-dichloro-6-methoxyhexanophenone O-(2-aminoethyl) oxime hydrochloride

The above entitled compound was obtained in an identical manner from 3', 4'-dichloro-6-methoxyhexanophenone oxime (melting point 53°–54.5° C) and 2-chloroethylamine hydrochloride. The melting point after recrystallization from ether/petroleum ether was 82°–84° C.

14. 3', 4'-dichloro-6-methoxyhexanophenone O-(2-amino-ethyl) oxime hydrochloride a. 25 mmol (1.10 g) of ethylene oxide were led into a solution of 15 mmol (4.4 g) of 3', 4'-dichloro-6-methoxyhexanophenone oxime (melting point 53°–54.5° C) in 25 ml of absolute ethanol, in which first 0.03 g of lithium had been dissolved, while stirring at 55° C and by means of a nitrogen flow, after which stirring was continued for another hour at 60° C. Subsequently, after the addition of 0.3 ml of acetic acid, the ethanol was distilled off in vacuo and the residue was purified chromatographically by means of silica gel with methylene chloride as an eluent. After evaporating the solvent, the O-(2-hydroxyethyl) oxime was obtained as an oil.

b. To a solution of 11 mmol (3.3 g) hereof in 60 ml of methylene-chloride were added while stirring and at −5° to 0° C 2.25 ml of triethylamine and then 12 mmol (0.9 ml) of mesyl chloride were added dropwise in approximately 20 minutes. After stirring at 0° C for another 30 minutes, the reaction mixture was washed successively with icy water, an icy-cold 5% sodium bicarbonate solution and an icy-cold saturated sodium chloride solution. After drying over sodium sulphate the methylene chloride was distilled off in vacuo. In this manner the 0-(mesyloxyethyl)oxime was obtained.

c. A mixture of 8 mmol (3.3 g) hereof in 30 ml of methanol which contained approximately 4 g of ammonia was kept at 100° C in an autoclave for 16 hours. After cooling, the methanol was removed in vacuo. The residue was stirred with 50 ml of 2N sodium hydroxide solution and extracted with ether. The ether layer was washed with a 5% sodium bicarbonate solution. After drying on sodium sulphate and distilling off the ether in vacuo, the resulting base was dissolved in alcoholic hydrochloric acid. After evaporating the ethanol, the above entitled compound crystallized from ether/petroleum ether (1 : 1). Melting point 82°–84° C.

15. 3', 4'-dichloro-4-cyanobutyrophenone 0-(2-aminoethyl) oxime hydrochloride.

The above entitled compound having a melting point of 129°–130° C (isopropanol/ether) was obtained in an identical manner from 3', 4'-dichloro-4- cyanobutyrophenone oxime (melting point 122°–123° C).

16. 3', 4'-dichloro-4-(2-methoxyethoxy) butyrophenone 0-(2-aminoethyl) oxime furmarate (1 : 1)

10 mmol (3.4 g) of 3', 4'-dichloro-4-(2-methoxyethoxy) butyrophenone ethylene ketal, 10 mmol (1.49 g) of 2-amino-oxyethylamine dihydrochloride and 10 ml of methanol were refluxed for 4 hours. The residue which was obtained after evaporating the methanol was dissolved in water and washed three times with ether. The aqueous solution after rendering alkaline with sodium hydroxide solution was extracted three times with methylene chloride. The combined extracts were washed with a 5% sodium bicarbonate solution and then with water. After drying on sodium sulphate and evaporating the methylene chloride, the free base was obtained. This was converted into the above entitled compound with an equimolar quantity of fumaric acid in ethanol. After crystallization from ethanol/acetonitrile 2/3, the melting point was 141°–143° C.

17. 3', 4'-dichloro-4-ethoxybutyrophenone 0-(2-aminoethyl)oxime hydrochloride In an identical manner, 3', 4'-dichloro-4-ethoxybutyrophenone ethylene ketal was converted with 2-amino-oxyethylamine dihydrochloride. The free base obtained after processing was converted into the above entitled compound with alcoholic hydrochloric acid. After crystallization from ether/petroleum ether the melting point was 92°–94° C.

18. 3', 4'-dichloro-5-methoxyvalerophenone 0-(2-aminoethyl) oxime hydrochloride 10 mmol (3.6 g) of 3', 4'- 5-trichlorovalerophenone 0-(2-aminoethyl) oxime hydrochloride (melting point 98°–99.5° C) was brought in a sodium methoxide solution (from 20 mmol sodium and methanol). This mixture was refluxed for 50 hours and then evaporated to dryness in vacuo. The resulting residue was treated with water and ether. The ether fraction was processed in the usual manner. The resulting base was converted with alcoholic hydrochloric acid. The above entitled compound obtained herefrom had a melting point of 93°–94° C after crystallization from ether/petroleum ether (1 : 1).

19. 3', 4'-dichloro-5-cyanovalerophenone 0-(2-aminoethyl) oxime hydrochloride.

10 mmol (3.6 g) of 3', 4', 5-trichlorovalerophenone 0-(2-aminoethyl) oxime hydrochloride (melting point 98°–99.5° C) were converted into the free base and this was heated at approximately 60° C while stirring for 3 hours together with 15 mmol (0.73 g) of sodium cyanide and 10 ml of dimethylsulphoxide. After cooling, the reaction mixture was diluted with 100 ml of water and then extracted three times with 40 ml of ether. The combined ether extracts were washed with water, dried over sodium sulphate and evaporated to dryness in vacuo. The residue was chromatographed over silica gel with ethanol/ammonia 95/5 as an eluent. After evaporating the solvents, the thus purified free base was converted into the hydrochloride with ethanolic hydrochloric acid. The melting point after crystallization from ethanol/ether was 134°–135° C.

20. 3', 4'-dichloro-3-(2-methoxyethoxy) propiophenone 0(2-aminoethyl) oxime maleate (1 : 1)

10 mmol (3.2 g) of 3'-amino-4'-chloro-3-(2-methoxy ethoxy) propiophenone 0-(2-aminoethyl) oxime were diazotised in 10 ml of 6N HCl at 0° C with a solution of 10 mmol (0.7 g) of sodium nitrite in 4 ml of water. This reaction mixture was stirred at 0° C for another hour and then added to a suspension of 1.1 g of cuprochloride in 10 ml of water of 75° C. The mixture was then cooled to room temperature after which 10 ml of 12N hydrochloric acid were added. The mixture was stirred for 2 hours and poured on 20 ml of 50% sodium hydroxide solution while cooling. The mixture was then extracted with ether and after washing with 5% sodium bicarbonate solution and water, the extracts were dried over sodium sulphate. The residue which was obtained after evaporation of the ether was chromatographed over silica gel with ethanol/ammonia 95/5 as an eluent. The thus purified free base was converted, with an equimolar quantity of maleic acid, into the above entitled compound which was obtained as a resin.

21. 3', 4'-dichloro-5-(2-methoxyethoxy) valerophenone 0-(2-aminoethyl) oxime fumarate (1 : 1)

In an identical manner, 3'-amino-4'-chloro-5-(2-methoxyethoxy) vaerophenone 0-(2-aminoethyl) oxime was converted. From this the above entitled compound was obtained having a melting point of 141°–143° C.

22. 3', 4'-dichloro-4-ethoxybutyrophenone 0-(2-amino-ethyl) oxime hydrochloride 24.7 mmol (1.00 ml) of methanol in 3 ml of tetrahydrofuran (T.H.F.) were added in 3 minutes to 7.8 mmol of LiAlH$_4$ in 10 ml of T.H.F. while stirring and cooling in icy water. While stirring and cooling, a solution of 1.15 mmol (0.36 g) of 3', 4'-dichloro-4-ethoxybutyrophenone 0-(cyanomethyl)oxime was added in 10 minutes. After stirring the reaction mixture at 5° C for another 3 hours, it was decomposed, with 1.0 ml of water. The formed hydroxides were sucked off, washed with chloroform and the filtrate was evaporated to dryness in vacuo. The resulting base was converted into the above entitled compound with alcoholic hydrochloric acid. The melting point after recrystallization from ether/petroleum ether was 92°–94° C.

23. Tablet 50 mg of 3', 4'-dichloro-4-cyanobutyrophenone 0-(2-amino-ethyl) oxime. HCl
335 mg of lactose
60 mg of potato starch
25 mg of talcum
5 mg of magnesium stearate
5 mg of gelatin

24. Suppository 50 mg of 3', 4'-dichloro-5-(cyano)valerophenone 0-(2-aminoethyl) oxime. HCl.
1500 mg of suppository mass

Injection liquid 25 g of 3', 4'-dichloro-6-cyanohexanophenone 0-(2-amino-ethyl)oxime. HCl.
1.80 g of methyl-p-hydroxybenzoate
0.20 g of propyl-p-hydroxybenzoate
9.0 g of sodium chloride 4.0 g of poly(oxyethylene)$_{20}$ sorbitan mono-oleate water up to 1000 ml.

We claim:

1. Compounds as represented by formula

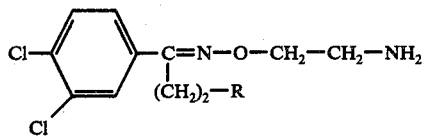 (I)

and salts thereof with pharmaceutically acceptable acids, in which formula R is the group $(CH_2)_pCN$, the group $(CH_2)_pO(CH_2)_qCH_3$ or the group $(CH_2)_rO(CH_2)_2OCH_3$, wherein $p = 1, 2$ or $3$, $q$ is $1$ if $p = 1$ and $q$ is $0$ if $p = 2$ or $3$ and $r = 0, 1$ or $2$.

2. The 3′, 4′-dichloro-4-ethoxybutyrophenone 0-(2-amino-ethyl) oxime and salts thereof with pharmaceutically acceptable acids of claim 1.

3. The 3′, 4′-dichloro-5-methoxyvalerophenone 0-(2-amino-ethyl) oxime and salts thereof with pharmaceutically acceptable acids of claim 1.

4. The 3′, 4′-dichloro-6-methoxyhexanophenone 0-(2-aminoethyl) oxime and salts thereof with pharmaceutically acceptable acids of claim 1.

5. The 3′, 4′-dichloro-3-(2-methoxyethoxy) propiophenone 0-(2-aminoethyl) oxime and salts thereof with pharmaceutically acceptable acids of claim 1.

6. The 3′, 4′-dichloro-4-(2-methoxyethoxy)-butyrophenone 0-(2-aminoethyl) oxime and salts thereof with pharmaceutically acceptable acids of claim 1.

7. The 3′, 4′-dichloro-5-(2-methoxyethoxy)valerophenone 0-(2-aminoethyl) oxime and salts thereof formed with pharmaceutically acceptable acids of claim 1.

8. A compound of the formula

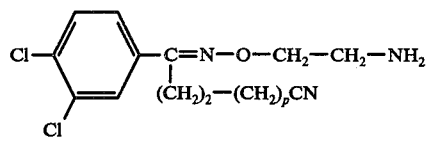

wherein $p = 1, 2$ or $3$ and salts thereof with pharmaceutically acceptable acids.

9. The 3′, 4′-dichloro-4-cyanobutyrophenone 0-(2-amino-ethyl)oxime and salts thereof with pharmaceutically acceptable acids of claim 8.

10. The 3′, 4′-dichloro-5-cyanovalerophenone 0-(2-amino-ethyl) oxime and salts thereof with pharmaceutically acceptable acids of claim 8.

11. The 3′, 4′-dichloro-6-cyanohexanophenone 0-(2-amino-ethyl) oxime and salts thereof with pharmaceutically acceptable acids of claim 8.

12. An antidepressive composition comprising an antidepressively effective compound of the formula

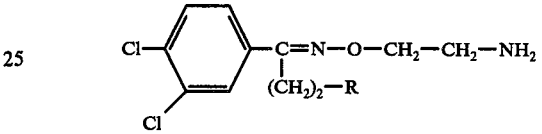

wherein R is $(CH_2)_pCN$ where $p$ is $1, 2$ or $3$ or a salt thereof formed with a pharmaceutically acceptable acid and a pharmaceutically acceptable carrier thereof.

13. A method of treating patients suffering from depression comprising administering to said patients an antidepressively effective quantity of a compound of the formula

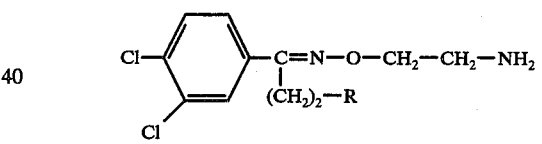

wherein R is $(CH_2)_pCN$ wherein $p$ is $1, 2$ or $3$ or a salt thereof formed with a pharmaceutically acceptable acid.

* * * * *